United States Patent
Lee et al.

(10) Patent No.: US 8,097,706 B2
(45) Date of Patent: Jan. 17, 2012

(54) METHODS FOR PREPARING CAPECITABINE AND BETA-ANOMER-RICH TRIALKYL CARBONATE COMPOUND USED THEREIN

(75) Inventors: Jaeheon Lee, Yongin-si (KR); Gha-Seung Park, Yongin-si (KR); Weon Ki Yang, Hwaseong-si (KR); Jin Hee Kim, Hwaseong-si (KR); Cheol Hyun Park, Seongnam-si (KR); Yong-Hoon An, Osan-si (KR); Yoon Ju Lee, Seoul (KR); Young-Kil Chang, Seoul (KR); Gwan Sun Lee, Seoul (KR)

(73) Assignee: Hanmi Holdings Co., Ltd, Seoul (KR)

( * ) Notice: Subject to any disclaimer, the term of this patent is extended or adjusted under 35 U.S.C. 154(b) by 74 days.

(21) Appl. No.: 12/742,367

(22) PCT Filed: Nov. 7, 2008

(86) PCT No.: PCT/KR2008/006565
§ 371 (c)(1),
(2), (4) Date: May 11, 2010

(87) PCT Pub. No.: WO2009/066892
PCT Pub. Date: May 28, 2009

(65) Prior Publication Data
US 2010/0249395 A1    Sep. 30, 2010

(30) Foreign Application Priority Data

Nov. 19, 2007    (KR) .................. 10-2007-0118062

(51) Int. Cl.
*C07G 3/00* (2006.01)
*C07G 11/00* (2006.01)
*C07H 15/00* (2006.01)
*C07H 17/00* (2006.01)
*C07H 19/00* (2006.01)

(52) U.S. Cl. ..................... 536/4.1; 536/27.11

(58) Field of Classification Search .................. None
See application file for complete search history.

(56) References Cited

U.S. PATENT DOCUMENTS

| 4,340,729 A | 7/1982 | D'Souza et al. |
| 5,272,949 A | 12/1993 | Holmes |
| 5,453,497 A | 9/1995 | Kamiya et al. |
| 5,472,949 A | 12/1995 | Arasaki et al. |
| 5,476,932 A | 12/1995 | Brinkman et al. |

FOREIGN PATENT DOCUMENTS

WO    WO2008/105593 A1 *  9/2008

OTHER PUBLICATIONS

Nobuo Shimma, et al., "The design and synthesis of a new tumor-selective fluoropyrimidine carbamate, Capecitabine," Bioorganic & Medicinal Chemistry, Jul. 2000, 1697-1706 (Abstract only), vol. 8, issue 7, English Abstract.
Fei et al., "Synthesis of [$^{18}$F]Xeloda as a Novel Potential PET Radiotracer for Imaging Enzymes in Cancers," Nuclear Medicine and Biology, 2004, vol. 31, pp. 1033-1041.
Wang et al., "Synthesis and Cytokine Modulation Properties of Pyrrolo [2,3-*d*-]4-pyrimidone Nucleosis," J. Med. Chem., 2000, vol. 43, pp. 2566-2574.
Kissman et al., "The Synthesis of Certain 5-Deoxy-D-ribofuranosylpurines," J. Am. Chem. Soc., 1957, vol. 79, pp. 5534-5540.
Sairam et al., "Synthesis of 1,2,3-tri-*O*-acetyl-5-deoxy-D-rubofuranose from D-ribose," Carbohydrate Research, 2003, vol. 338, pp. 303-306.

* cited by examiner

*Primary Examiner* — Lawrence E Crane
(74) *Attorney, Agent, or Firm* — Sughrue Mion, PLLC

(57) ABSTRACT

The present invention relates to a method for preparing capecitabine and a method for preparing a β-anomer-rich trialkyl carbonate compound used therein, and a highly pure capecitabine can be efficiently prepared with a high yield by the method of the present invention using the β-anomer-rich trialkyl carbonate compound as an intermediate.

7 Claims, No Drawings

METHODS FOR PREPARING CAPECITABINE AND BETA-ANOMER-RICH TRIALKYL CARBONATE COMPOUND USED THEREIN

CROSS REFERENCE TO RELATED APPLICATIONS

This application is a National Stage of International Application No. PCT/KR2008/006565 filed Nov. 7, 2008, claiming priority based on Korean Patent Application No. 10-2007-0118062, filed Nov. 19, 2007, the contents of all of which are incorporated herein by reference in their entirety.

FIELD OF THE INVENTION

The present invention relates to a method for preparing capecitabine as well as a method for preparing a β-anomer-rich trialkyl carbonate compound used therein.

BACKGROUND OF THE INVENTION

Capecitabine is an orally-administered anticancer agent widely used in the treatment of metastatic breast and colorectal cancers. Capecitabine is a ribofuranose-based nucleoside, and has the stereochemical structure of a ribofuranose having an β-oriented 5-fluorocytosine moiety at C-1 position.

U.S. Pat. Nos. 5,472,949 and 5,453,497 disclose a method for preparing capecitabine by glycosylating tri-O-acetyl-5-deoxy-β-D-ribofuranose of formula I using 5-fluorocytosine to obtain cytidine of formula II; and carbamoylating and hydrolyzing the resulting compound, as shown in Reaction Scheme 1:

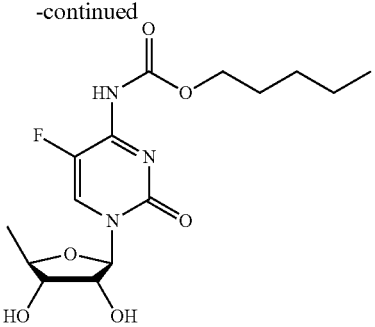

The compound of formula I employed as an intermediate in Reaction Scheme 1 is the isomer having a β-oriented acetyl group at the 1-position, for the reason that 5-fluorocytosine is more reactive toward the β-isomer than the α-isomer in the glycosylation reaction due to the occurrence of a significant neighboring group participation effect which takes place when the protecting group of the 2-hydroxy group is acyl.

Accordingly, β-oriented tri-O-acetyl-5-deoxy-β-D-ribofuranose (formula I) has been regarded in the conventional art to the essential intermediate for the preparation of capecitabine. However, such a reaction gives a mixture of β- and α-isomers from which cytidine (formula II) must be isolated by an uneconomical step.

Meanwhile, U.S. Pat. No. 4,340,729 teaches a method for obtaining capecitabine by the procedure shown in Reaction Scheme 2, which comprises hydrolyzing 1-methyl-acetonide of formula III to obtain a triol of formula IV; acetylating the compound of formula IV using anhydrous acetic anhydride in pyridine to obtain a β-/α-anomeric mixture of tri-O-acetyl-5-deoxy-D-ribofuranose of formula V; conducting vacuum distillation to purify the β-/α-anomeric mixture; and isolating the β-anomer of formula I therefrom:

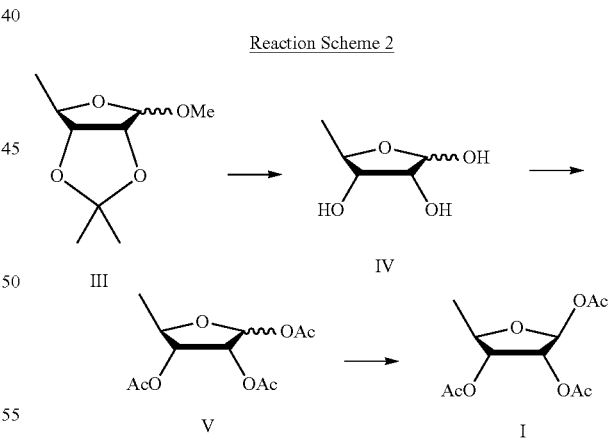

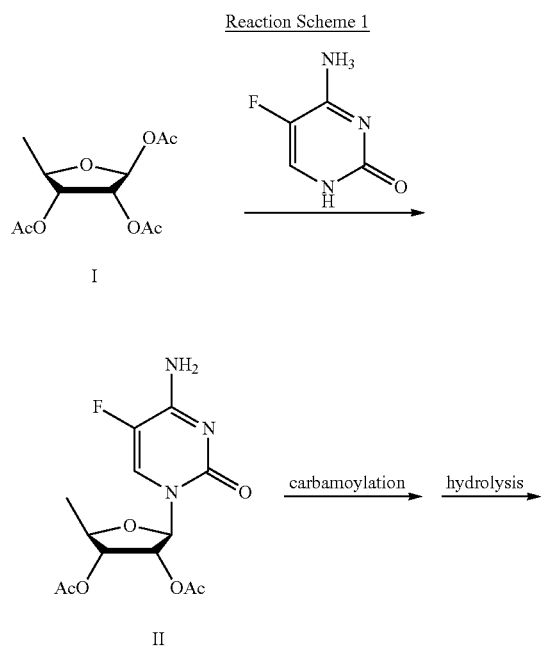

However, the above method is also hampered by the requirement to perform an uneconomical and complicated recrystallization steps for isolating the β-anomer from the mixture of β-/α-anomers of formula V, which leads to a low yield of only about 35% to 40% (Guangyi Wang et al., *J. Med. Chem.*, 2000, vol. 43, 2566-2574; Pothukuchi Sairam et al., *Carbohydrate Research*, 2003, vol. 338, 303-306; Xiangshu Fei et al., *Nuclear Medicine and Biology*, 2004, vol. 31, 1033-1041; and Henry M. Kissman et al., *J. Am. Chem. Soc.*, 1957, vol. 79, 5534-5540).

Further, U.S. Pat. No. 5,476,932 discloses a method for preparing capecitabine by subjecting 5'-deoxy-5-fluorocytidine of formula VI to a reaction with pentylchloroformate to obtain the compound of formula VII having the amino group and the 2-, 3-hydroxy groups protected with $C_5H_{11}CO_2$ groups; and removing the hydroxy-protecting groups from the resulting compound, as shown in Reaction Scheme 3:

Reaction Scheme 3

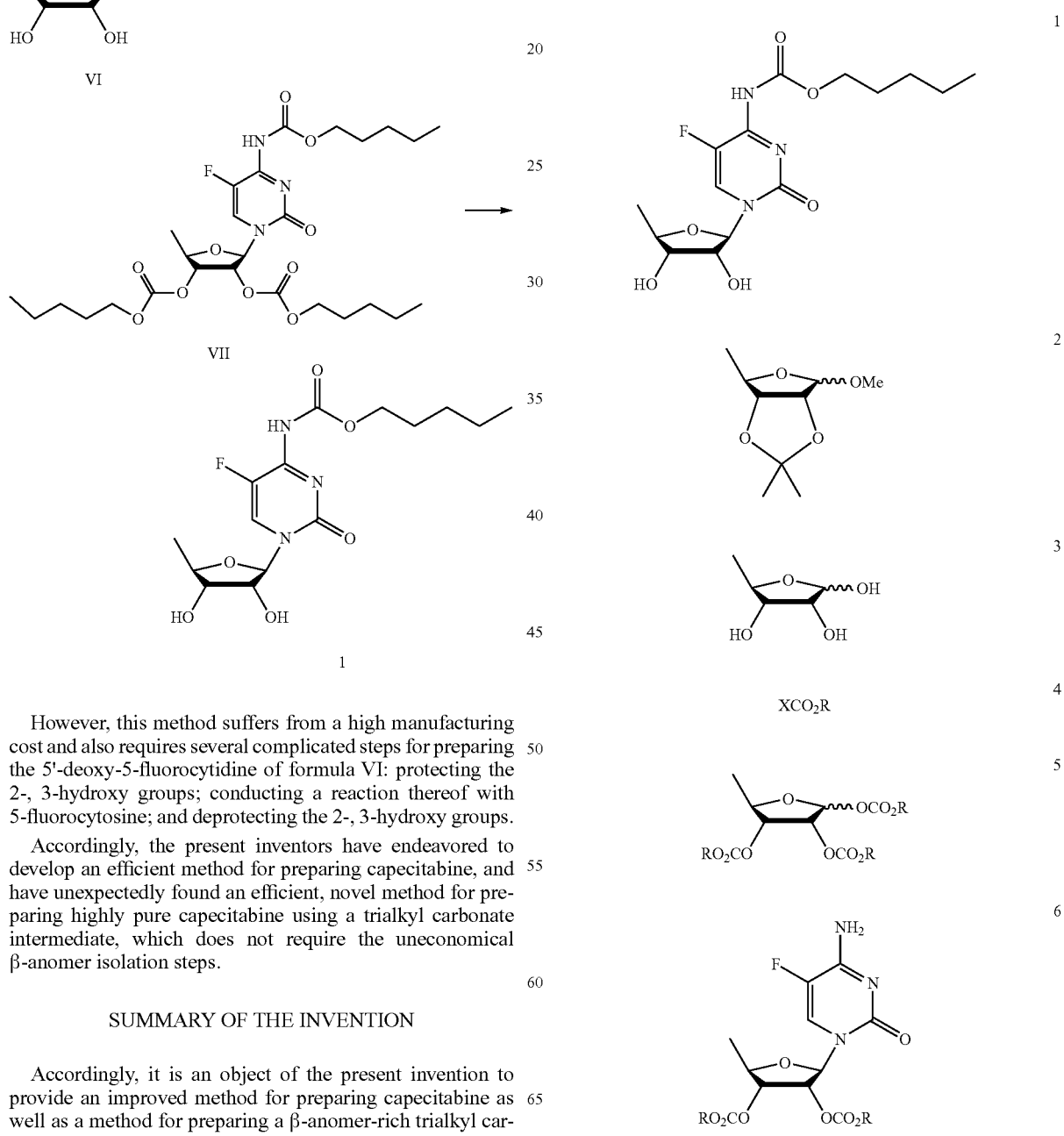

However, this method suffers from a high manufacturing cost and also requires several complicated steps for preparing the 5'-deoxy-5-fluorocytidine of formula VI: protecting the 2-, 3-hydroxy groups; conducting a reaction thereof with 5-fluorocytosine; and deprotecting the 2-, 3-hydroxy groups.

Accordingly, the present inventors have endeavored to develop an efficient method for preparing capecitabine, and have unexpectedly found an efficient, novel method for preparing highly pure capecitabine using a trialkyl carbonate intermediate, which does not require the uneconomical β-anomer isolation steps.

SUMMARY OF THE INVENTION

Accordingly, it is an object of the present invention to provide an improved method for preparing capecitabine as well as a method for preparing a β-anomer-rich trialkyl carbonate which can be used as an intermediate in said method.

In accordance with one aspect of the present invention, there is provided a method for preparing capecitabine of formula 1, comprising the steps of (1) hydrolyzing a methylacetonide compound of formula 2 to obtain a triol compound of formula 3; (2) reacting the compound of formula 3 with an haloalkyl formate of formula 4 in the presence of mixture of pyridine and triethylamine to obtain a β-anomer-rich trialkyl carbonate compound of formula 5; (3) conducting a glycosylation of the compound of formula 5 using 5-fluorocytosine in the presence of an acid to obtain a dialkoxycarbonyl cytidine compound of formula 6; (4) performing carbamoylation of the compound of formula 6 using n-pentyl chloroformate to obtain a carbamoylcytidine compound of formula 7; and (5) deprotecting the carbonate hydroxy protecting groups of the compound of formula 7:

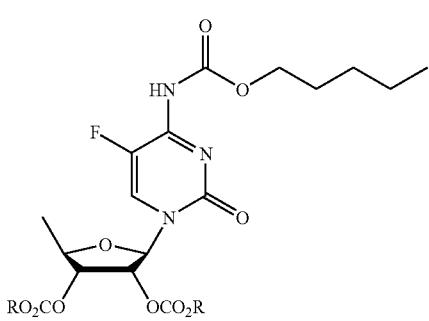

7 wherein, X is chloro, bromo or iodo; and R is methyl or ethyl.

In accordance with another aspect of the present invention, there is provided a method for preparing a trialkyl carbonate compound of formula 5 used as an intermediate in said method:

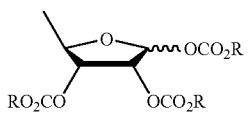

5 wherein, R has the same meaning as defined above.

DETAILED DESCRIPTION OF THE INVENTION

In the present invention, the trialkyl carbonate compound of formula 5 is a 2:1 to 4:1 mixture of the β- and α-anomers, which can be used to prepare highly pure capecitabine of formula 1 in a high yield through an improved glycosylation procedure of the trialkyl carbonate intermediate using 5-fluorocytosine.

The inventive method for preparing capecitabine is summarized in Reaction Scheme 4:

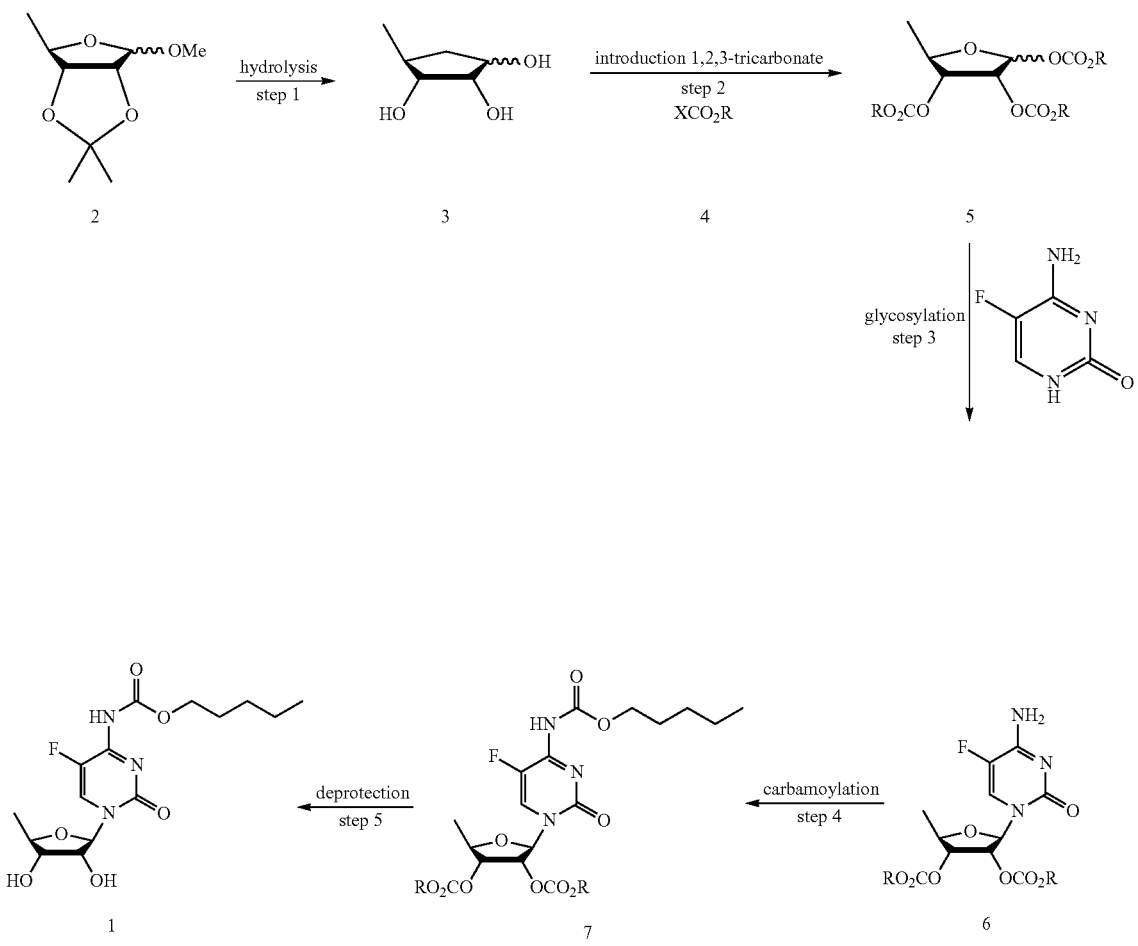

wherein, X and R have the same meanings as defined above.

Hereinafter, the steps of the inventive method shown in Reaction Scheme 4 are described in detail as follows:

<Step 1>

In step 1, the triol compound of formula 3 may be prepared by hydrolyzing the methyl acetonide compound of formula 2 in a solvent such as an aqueous sulfuric acid according to the conventional method described in U.S. Pat. No. 4,340,729. The method of the present invention may further optionally comprise a process for isolating each of the anomers of the resulting triol compound.

<Step 2>

In step 2, the β-anomer-rich trialkyl carbonate compound of formula 5 may be obtained by allowing the triol compound obtained in step 1 to react with the haloalkyl formate compound of formula 4 in a solvent in the presence of a base, preferably an organic base such as pyridine, triethylamine and a mixture thereof. The resulting compound obtained is a β-anomer-rich trialkyl carbonate of formula 5, which undergoes rapid glycosylation in step 3 because the β-anomer is more reactive than α-anomer.

When the carbonation of the triol compound is conducted in the presence of pyridine only, the resulting compound may be of the form of a 1:1 mixture of α- and β-anomers or an α-anomer-rich mixture. Further, if the carbonation is performed in the presence of triethylamine only, the resulting compound may be a highly β-anomer-rich mixture having a β-anomer:α-anomer ratio of as high as 6:1 depending on the reaction temperature and the equivalent thereof. However, such carbonation using only triethylamine has a problem that a side product of the compound of formula 1a may be formed in an excessive amount:

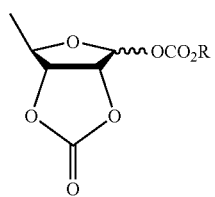

1a wherein, R has the same meaning as defined above.

In the present invention, a mixture of pyridine and triethylamine having a specific mixing ratio may be employed as a base in this carbonation reaction of the triol compound, which makes it possible to obtain the β-anomer-rich compound of formula 5, the content of which is more than twice the amount of the α-anomer, while minimizing the formation of impurities, e.g., the cyclic carbonate compound of formula 1a. Especially, when the reaction is conducted in the presence of a mixture of pyridine and triethylamine at a low temperature, the content of the cyclic carbonate compound in the reaction product can be reduced less than 0.2%.

In the present invention, pyridine used in the mixture may be employed in an amount ranging from 1 to 2 equivalents, preferably 1.3 to 1.6 equivalents based on triethylamine. Further, the mixture of pyridine and triethylamine may be employed in an amount ranging from 4 to 10 equivalents, preferably 4 to 6 equivalents based on the triol compound.

The solvent may be dichloromethane, dichloroethane, chloroform, tetrahydrofuran, acetonitrile, dimethylformamide or a mixture thereof, preferably dichloromethane.

The haloalkyl formate compound of formula 4 may be employed in an amount ranging from 3 to 10 equivalents, preferably 5 to 7 equivalents based on the triol compound.

Preferably, the above reaction may be conducted at a temperature of −50 to −30° C., preferably −35 to −30° C., because the cyclic carbonate compound can be formed in an excessive amount when the reaction is carried out at a temperature above −30° C.

<Step 3>

In step 3, the dialkoxycarbonyl cytidine compound (formula 6) may be prepared by conducting glycosylation of the compound obtained in step 2 using 5-fluorocytosine in a solvent in the presence of an acid.

In the above reaction, in order to solve the competitive reaction of the amino groups onto 1-anomeric position, it is preferred to use a silylated derivative of 5-fluorocytosine obtained by reacting 5-fluorocytosine with a silylating agent such as hexamethyldisilazane according to a conventional method, instead of 5-fluorocytosine. 5-Fluorocytosine or its silylated derivative may be employed in an amount ranging from 1 to 2 equivalents, preferably 1 equivalent based on the trialkyl carbonate compound of formula 5.

The acid is used for accelerating the glycosylation, and representative examples of the acid may include ethylaluminumdichloride, methylaluminumdichloride, SnCl$_4$, trimethylsilyl trifluoromethanesulfonate and trifluoromethanesulfonic acid, preferably trimethylsilyl trifluoromethanesulfonic acid. Further, the acid may be employed in an amount ranging from 0.5 to 3 equivalents, preferably 1 equivalent based on the trialkyl carbonate compound of formula 5.

In the present invention, the solvent used in the above reaction may be ethyl acetate, dichloromethane, dichloroethane, chloroform, tetrahydrofuran, acetonitrile or dimethylformamide, preferably acetonitrile, and the reaction may be conducted at a temperature of 0 to 50° C., preferably 20 to 35° C.

In the present invention, the dialkoxycarbonyl cytidine compound of formula 6 may be obtained from the β-anomer-rich trialkyl carbonate compound of formula 5 in an improved yield more than 10% relative to the convention method using tri-O-acetyl-5-deoxy-β-D-ribofuranose (formula I), e.g., a high yield of more than 90%, via the glycosylation. Especially, the compound of formula 6 obtained in the inventive method has a high purity of more than 98.5%. Further, due to the use of such a highly pure compound with a high yield in following steps of the inventive method, it is possible to obtain the final product, capecitabine, having a high purity of 99.5%.

<Step 4>

In step 4, the carbamoyl cytidine compound of formula 7 may be prepared by performing carbamoylation of the dialkoxycarbonyl cytidine compound obtained in step 3 using n-pentyl chloroformate in a solvent in accordance with a conventional method.

In this reaction, n-pentyl chloroformate may be employed in an amount ranging from 1 to 3 equivalents, preferably 1.1 to 1.5 equivalents based on the dialkoxycarbonyl cytidine compound of formula 6.

The solvent may be an organic solvent such as chloroform, dichloromethane, dichloroethane, tetrahydrofuran and acetonitrile, preferably dichloromethane.

Meanwhile, during the carbamoylation, an organic base such as triethylamine and pyridine may be added to the reaction mixture so as to neutralize hydrochloric acid generated therein, and the organic base may be employed in an amount ranging from 1 to 5 equivalents, preferably 1.3 to 2.5 equivalents based on the dialkoxycarbonyl cytidine compound of formula 6.

The above reaction may be conducted at a temperature of −10 to 10° C., preferably −5 to 5° C.

The carbamoylation may be quantitatively conducted, and it is preferred that the product thereof is used in the following step without undergoing an isolation process.

<Step 5>

In step 5, capecitabine of formula 1 may be prepared by removing the carbonate hydroxyl protecting groups from the carbamoyl cytidine compound obtained in step 4 according to a conventional method.

In accordance with a conventional method described in Theodora W. Green, *Green's protective groups in organic synthesis, fourth edition*, 2007, pages 280, 998 and 1022, Wiley-Interscience, in case of coexisting carbonate hydroxy protecting groups with carbamate protecting groups in a compound, the carbonate protecting groups can be selectively removed by controlling the reaction temperature and the concentration of a base used therein. This selective deprotection is based on the difference between the reactivities of the carbonate and carbamate protecting groups, in that a carbonate group can be deprotected even at pH 10 and a room temperature while the deprotection of a carbamate group requires a high pH of more than 12 and a high reaction temperature of more than 100° C.

In the present invention, the selective deprotection may be conducted in an organic solvent such as a mixture of methanol and water (2:1 (v/v)) in the presence of a base including sodium hydroxide and sodium carbonate at a temperature of −10 to 0° C., preferably −5 to 0° C.

Accordingly, according to the method of the present invention using a β-anomer-rich trialkyl carbonate compound containing β-anomer more than twice as much as α-anomer as an intermediate, it is possible to obtain capecitabine exhibiting a high purity of more than 99% without an uneconomical β-anomer isolation process. Further, the inventive method exhibits a high total yield of 90% in step 4 and step 5.

The following Examples are intended to further illustrate the present invention without limiting its scope.

EXAMPLE 1

Preparation of 1,2,3-tri-O-methoxycarbonyl-5-deoxy-D-ribofuranose (a Compound of Formula 5)

20 g of methyl-2,3-O-isopropylidene-5-deoxy-D-ribofuranose was dissolved in 100 ml of 2 mol % aqueous sulfuric acid, and the mixture was stirred at 80 to 85° C. for 2 hrs. The reaction mixture was cooled to room temperature, and concentrated under a reduced pressure to remove about one third to a half of the solvent. Added to the resulting concentrate was 100 ml of 2 mol % aqueous sulfuric acid, the resulting mixture was stirred at about 80 to 85° C. for 1 hr, cooled to room temperature, and sodium hydrogen carbonate was added thereto until the pH of the mixture became 3.0 to 3.5. The resulting solution was concentrated under a reduced pressure, mixed with 100 ml of acetonitrile and 20 g of anhydrous sodium sulfate followed stirring for 30 min, filtered, and the filtrate was concentrated under a reduced pressure to obtain 5-deoxy-D-ribofuranose.

14.3 g (0.107 mole) of 5-deoxy-D-ribofuranose was added to 200 ml of dichloromethane, 30.1 ml (0.372 mole) of pyridine and 37 ml (0.266 mole) of triethylamine were added thereto, and the mixture was cooled to −30° C. 49.1 ml (0.638 mole) of methyl chloroformate was added dropwise thereto at −30° C. over 30 min, the reaction mixture was warmed to 10° C., 100 ml of water was added thereto, and the resulting mixture was stirred for 30 min. The organic layer was separated, and successively washed with 200 ml of 1 N HCl, aqueous sodium bicarbonate and aqueous NaCl. The resulting organic layer was dried over anhydrous sodium sulfate, filtered, and the solvent was removed therefrom, to obtain 27.7 g of the title compound.

β-anomer:α-anomer=2.7:1

NMR characteristics of the β-anomer: $^1$H NMR(300 MHz, CDCl$_3$): δ 1.42(d, 3H), 3.82(s, 9H), 4.34~4.41(m, 1H), 5.00 (dd, 1H), 5.28(dd, 1H), 6.07(s, 1H).

NMR characteristics of the α-anomer: $^1$H NMR(300 MHz, CDCl$_3$): δ 1.37(d, 3H), 3.81(s, 9H), 4.40~4.48(m, 1H), 4.90 (dd, 1H), 5.17(dd, 1H), 6.29(d, 1H).

EXAMPLE 2

Preparation of 2',3'-di-O-methoxycarbonyl-5'-deoxy-5-fluorocytidine (a Compound of Formula 6)

11.6 g (0.090 mole) of 5-fluorocytosine, 19 ml of hexamethyldisilazane and 24 ml of acetonitrile were mixed, and 0.2 g of ammonium sulfate was added to the mixture, which was refluxed for 1 hr. After cooling the reaction mixture to room temperature, 72 ml of acetonitrile was added thereto, followed by subjecting the resulting mixture to distillation to remove about 60 ml of the solvent. The resulting solution was cooled to room temperature, mixed with 27.7 g (0.090 mole) of the compound obtained in Example 1 and 72 ml of acetonitrile, and the resulting mixture was cooled to 20° C. After adding 16.3 ml (0.090 mole) of trimethylsilyl trifluoromethanesulfonate dropwise thereto at 25° C., the reaction mixture was stirred at room temperature overnight, cooled to 10° C., mixed with 45.4 g of sodium hydrogen carbonate, and stirred for 30 min. 9.8 g of water and 72 ml of dichloromethane were added dropwise thereto, the resulting solution was stirred for 2 hrs, filtered, and the isolated solid was washed with 72 ml of dichloromethane. The filtrate was washed with 120 ml of 4% sodium bicarbonate, dried over anhydrous sodium sulfate, filtered, and concentrated under a reduced pressure, to obtain 35.8 g of the title compound.

$^1$H NMR(CDCl$_3$): δ 1.47(3H, d), 3.79(3H, s), 3.81(3H, s), 4.22~4.30(1H, m), 4.94(1H, dd), 5.39(1H, dd), 5.76(1H, d), 6.00(1H, br s), 7.37(1H, d), 8.78(1H, br s).

EXAMPLE 3

Preparation of 2',3'-di-O-methoxycarbonyl-5'-deoxy-5-fluoro-N$^4$-(pentyloxycarbonyl) cytidine (a Compound of Formula 7)

35.8 g (0.099 mole) of the compound obtained in Example 2 was mixed with 163 ml of dichloromethane and 11 ml (0.136 mole) of pyridine, and stirred. After cooling the resulting mixture to −5 to 0° C., 15.7 ml (0.109 mole) of n-pentyl chloroformate was added dropwise thereto while maintaining the temperature of the reaction mixture at less than 0° C., followed adding the resulting mixture was warmed to room temperature and stirred for 2 hrs, 1 N HCl thereto. The organic layer was separated, successively washed with 163 ml of saturated sodium bicarbonate and 163 ml of water, dried over anhydrous sodium sulfate, and concentrated under a reduced pressure, to obtain 42.9 g of the title compound.

$^1$H NMR(CDCl$_3$) δ 0.91(3H, t), 1.33~1.40(4H, m), 1.48 (3H, d), 1.69~1.74(2H, m), 3.82(6H, s), 4.16(2H, t), 4.27~4.32(1H, m), 4.93(1H, dd), 5.32(1H, dd), 5.83(1H, d), 7.40(1H, s), 12.02(1H, br s).

EXAMPLE 4

Preparation of 5'-deoxy-5-fluoro-N$^4$-(pentyloxycarbonyl)cytidine (the Compound of Formula 1)

42.9 g of the compound obtained in Example 3 was added to 215 ml of methanol, and the mixture was stirred and cooled to −5 to 0° C. 10.8 g of NaOH was dissolved in 107 ml of water, and NaOH solution was added thereto while maintaining the reaction mixture temperature at less than 0° C. The resulting mixture was stirred for 30 min, and 48 ml of 6 N HCl was added dropwise thereto until the pH of the reaction mixture became 5.3. The resulting mixture was successively washed twice with 215 ml of dichloromethane and once with 108 ml of dichloromethane, and the combined organic layer was washed with 215 ml of water, dried over anhydrous sodium sulfate, filtered and concentrated under a reduced pressure. After adding 129 ml of ethylacetate thereto, the residue was mixed with 97 ml of ethylacetate by stirring to be crystallized. 97 ml of hexane was added dropwise thereto to allow the crystal to be matured, and the resulting mixture was stirred for 1 hr, cooled to 0° C. and again stirred for 1 hr. The resulting solid was filtered, washed with 86 ml of a solid mixture of ethylacetate and hexane (1:1 (v/v)) cooled to 0° C., and dried in a 35° C. vacuum oven overnight, to obtain 28.6 g of the title compound as a light white solid.

$^1$H NMR(CD$_3$OD) δ 0.91(3H, t), 1.36~1.40(4H, m), 1.41 (3H, d), 1.68~1.73(2H, m), 3.72(1H, dd), 4.08(1H, dd), 4.13~4.21(3H, m), 5.70(1H, s), 7.96(1H, d)

While the invention has been described with respect to the above specific embodiments, it should be recognized that various modifications and changes may be made to the invention by those skilled in the art which also fall within the scope of the invention as defined by the appended claims.

What is claimed is:

1. A method for preparing capecitabine of formula 1, comprising the steps of:
   (1) hydrolyzing a methylacetonide compound of formula 2 to obtain a triol compound of formula 3;
   (2) reacting the compound of formula 3 with an haloalkyl formate of formula 4 in the presence of mixture of pyridine and triethylamine to obtain a β-anomer-rich trialkyl carbonate compound of formula 5;
   (3) conducting a glycosylation of the compound of formula 5 using 5-fluorocytosine in the presence of an acid to obtain a dialkoxycarbonyl cytidine compound of formula 6;
   (4) performing carbamoylation of the compound of formula 6 using n-pentyl chloroformate to obtain a carbamoylcytidine compound of formula 7; and
   (5) deprotecting the carbonate hydroxy protecting groups of the compound of formula 7:

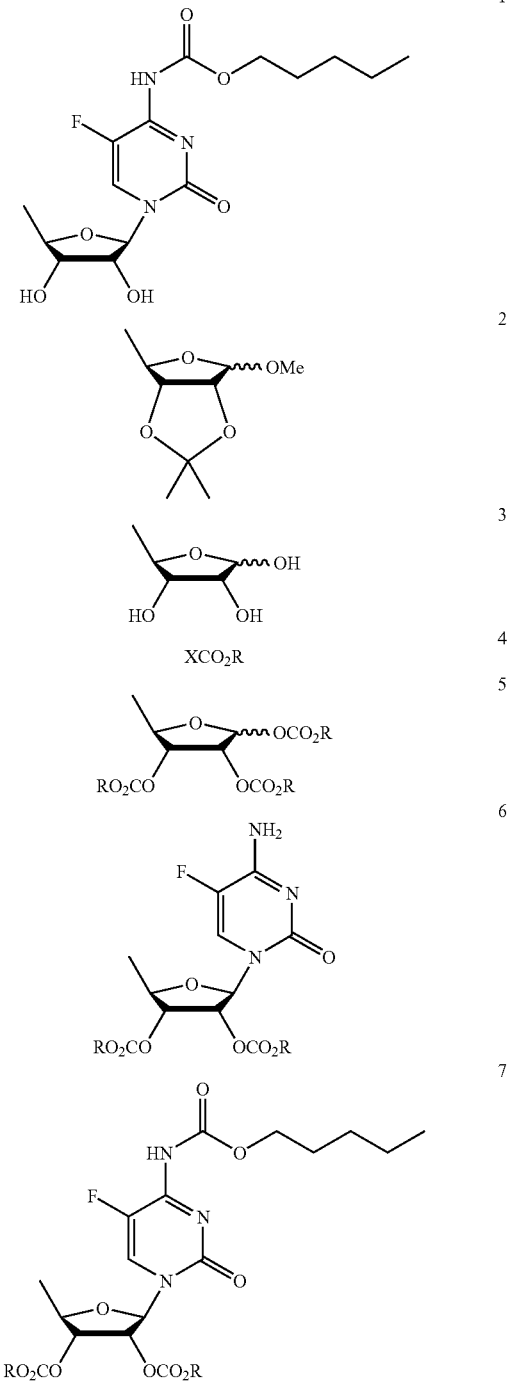

wherein,
X is chloro, bromo or iodo; and
R is methyl or ethyl.

2. A method for preparing a trialkyl carbonate compound of formula 5, comprising the steps of:
   (1) hydrolyzing a methylacetonide compound of formula 2 to obtain a triol compound of formula 3; and
   (2) letting the compound of formula 3 react with a haloalkyl formate of formula 4 in the presence of a mixture of pyridine and triethylamine to obtain a β-anomer-rich trialkyl carbonate of formula 5:

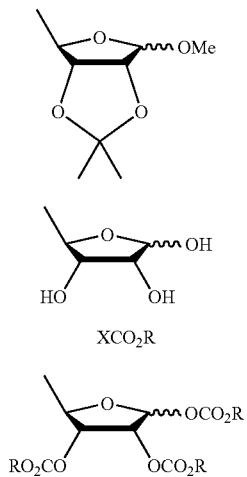

wherein, X and R have the same meanings as defined in claim 1.

3. The method of claim 2, wherein pyridine is employed in an amount ranging from 1 to 2 equivalents based on triethylamine.

4. The method of claim 2, wherein the mixture of pyridine and triethylamine is employed in an amount ranging from 4 to 10 equivalents based on the compound of formula 3.

5. The method of claim 2, wherein the reaction in step (2) is conducted at a temperature of −50 to −30° C.

6. The method of claim 1, wherein the acid employed in step (3) is ethylaluminumdichloride, methylaluminumdichloride, SnCl₄, trimethylsilyl trifluoromethanesulfonic acid or trifluoromethanesulfonate.

7. The method of claim 6, wherein the acid is employed in an amount ranging from 0.5 to 3 equivalents based on the compound of formula 5.

* * * * *